United States Patent [19]
Stef

[11] Patent Number: 5,209,750
[45] Date of Patent: May 11, 1993

[54] EXTERNAL HOLDING AND REDUCING BRACE FOR BONE FRACTURES

[75] Inventor: Francine Stef, Charleville Mezieres, France

[73] Assignee: Compagnie General de Materiel Orthopedique, France

[21] Appl. No.: 775,197

[22] Filed: Oct. 11, 1991

[30] Foreign Application Priority Data

Oct. 12, 1990 [FR] France ................... 90 12856

[51] Int. Cl.⁵ .......................................... A61B 17/56
[52] U.S. Cl. ............................................ 606/54; 606/59
[58] Field of Search .................................... 606/53-59

[56] References Cited

U.S. PATENT DOCUMENTS

| | | | |
|---|---|---|---|
| 4,135,505 | 1/1979 | Day | 606/54 |
| 4,554,915 | 11/1985 | Brumfield | 606/54 |
| 4,621,627 | 11/1986 | DeBastiani | 606/54 |
| 4,624,249 | 11/1986 | Alvarez Cambras | 606/54 |
| 4,662,365 | 5/1987 | Gotzen | 606/54 |
| 4,889,111 | 12/1989 | Ben-Dov | 606/54 |
| 4,919,119 | 4/1990 | Jonsson | 606/54 |
| 4,998,935 | 3/1991 | Pennig | 606/54 |
| 5,019,077 | 5/1991 | De Bastiani | 606/54 |
| 5,026,372 | 6/1991 | Sturtzkopf | 606/54 |
| 5,041,112 | 8/1991 | Mingozzi | 606/59 |
| 5,062,844 | 11/1991 | Jamison | 606/54 |

Primary Examiner—Robert A. Hafer
Assistant Examiner—Michael Brown
Attorney, Agent, or Firm—Pravel, Hewitt, Kimball & Krieger

[57] ABSTRACT

An orthopedic brace for the reduction of long-bone fractures, which includes telescopic components (7, 8) which are made of an X-ray transparent material and form two transverse plates (9 and 10) at their opposite ends. A locking device (11) is composed of a slide (12) working in conjunction with two chucks (13 and 14) fitted to the periphery of the plates and position-adjusting devices for each flange are made up of three threaded rods (40) angularly equidistant, individually adjustable as to length and mounted in the corresponding plate by means of three ball-and-socket joints.

27 Claims, 6 Drawing Sheets

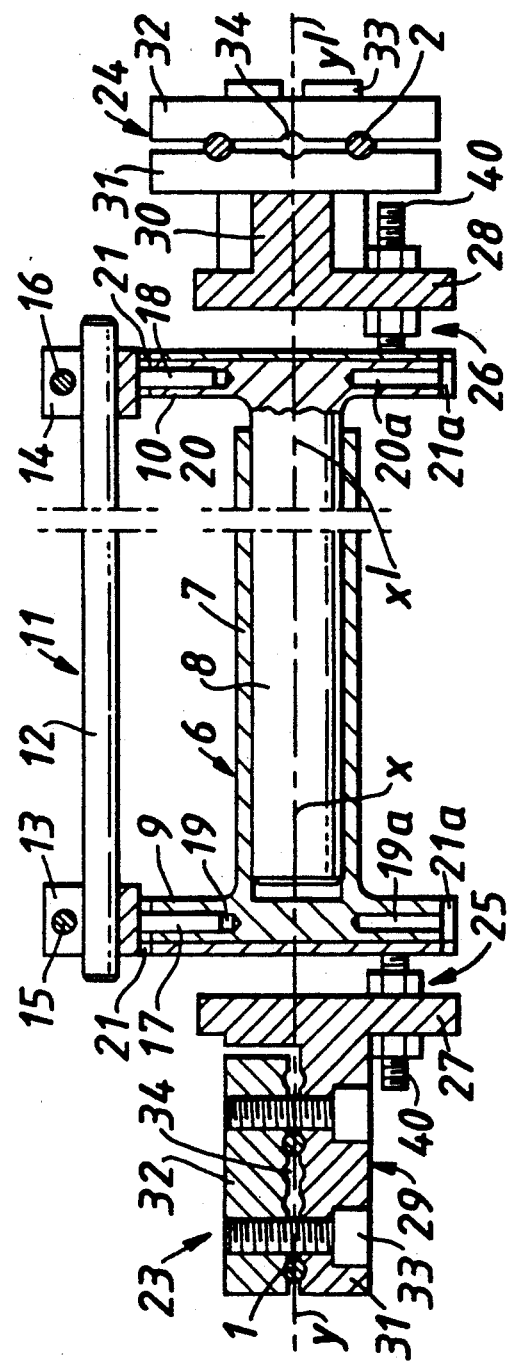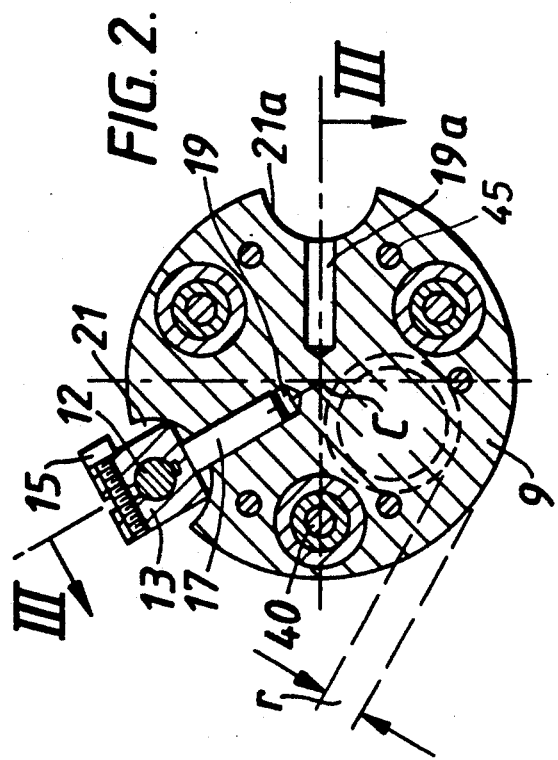

EXTERNAL HOLDING AND REDUCING BRACE FOR BONE FRACTURES

BACKGROUND OF THE INVENTION

This invention is related to orthopedic equipment and concerns, more particularly, equipment intended to permit the reduction and knitting of bone fractures by holding and realignment, especially those of the lower and upper limbs.

The invention essentially concerns external orthopedic holding appliances as compared to internal holding appliances made up, for example, of screwed plates, pins, etc.

If orthopedic reducing devices fastening internally do certainly make it possible to achieve the result of reduction and knitting of a fracture, it is clear that the use of them involves an invasive method, seeing that the practitioner is forced to open up the traumatized limb to reach and free the fractured bone in order to be able to fit a plate, strip or pin attached by screws implanted in bony material to the segments of that bone. So it is a matter of a surgical operation which may be awkward, with the consequences which may attend such practices even if these are generally well mastered.

The object of external orthopedic holding devices is to eliminate such a surgical operation by implanting directly a kind of external lateral harness, by means of pins passing through the flesh and fixed in the bone segments, insuring the immobilization of the fractured bone segments in the position required.

Prior art is familiar with various proposals to this effect. By way of indication one may mention the ILIZAROF external fastening device, the main drawback of which is the need to use a large number of through pins which are implanted in different directions in the bone, passing through the flesh. The use of such a fastening device is extremely delicate, since, in order to implant the various pins, it is absolutely necessary to insure that they pass between the muscles without traumatizing the nerves, tendons or arterial and venous systems.

Also known in prior art is an external fastening system known as that of HOFFMANN, using, between the through pins for fastening, connecting and supporting devices which are relatively clumsy and difficult to adjust.

There was a development in simplicity of design with the OSTEO external holding appliance, composed of two telescopic parts adjustable relative to each other, the ends of which are equipped with devices for locking and orienting through pins. If such a device unquestionably represents a simplification of previous appliances, consideration must be given to the fact that the proposal formulated leads to a clumsy appliance with little possibility of simple, quick and easy adjustment of the direction of the fin-locking devices to correspond to the preferred direction of implantation of those pins.

It is also appropriate to mention another suggestion known by the name of dynamic axial attachment system proposed by the ORTHOFIX Company. Such an appliance is composed of an elongated support of adjustable length, the ends of which are equipped with position-adjusting devices for two end flanges connected to through pins. The position-adjusting devices at each end are composed of a locking pin which proves in practice to allow a certain amount of slippage, irremediably and detrimentally modifying the relative alignment between the fractured segments of a bone to be reduced and knit together.

The purpose of the invention is to respond to the problem posed by the external attachment (of fractured bone segments by proposing a new brace of light, but sturdy design which can be adjusted in a rapid, sure and durable manner, as regards both length and position adjustment, so as to offer every possibility of adaptation to preferred directions or through pins which have to be immobilized relatively to insure the proper and correct alignment of fractured segments, then, maintenance in a reduced state and their knitting together over time.

Another purpose of the invention is, by simple adaptation, to permit a relative, limited, elastic cushioning function, when, for example, there is a need to have the brace perform a possible function of alternate compression of the line of fracture so as to reinforce over time the knitting together being established.

Another purpose of the invention is also to make it possible to have the external brace assume, if need be, a function of elongation when such a method has to be applied, which is itself familiar in any case.

Another purpose of the invention is to propose a new brace with relatively little bulk so as to allow external fitting close to the traumatized limb.

A further purpose of the invention is to offer a brace allowing X-ray photographs to be taken without dismantling, without its components being obstacles concealing the bony parts to be X-rayed.

In order to attain the above objectives, the external brace according to the invention is characterized by the fact that

- the telescopic parts are of an X-ray transparent material and form two transverse plates at their opposite ends;
- the locking mechanism consists of a slide working in conjunction with two collet chucks fitting the periphery of the plates;
- in the case of each flange, the position-adjusting devices are made up of three threaded rods at equidistant angles, individually adjustable in length and mounted in the corresponding plate with three ball-and-socket joints to extend, in the neutral position, parallel to tie axis of the telescopic elements.

BRIEF DESCRIPTION OF THE DRAWINGS

Various other features of the subject of the invention are apparent from the description below referring to the attached drawings, which show, as nonlimitative examples, applications of the subject of the invention.

FIG. 2 is a cross section along line II—II of FIG. 1.

FIG. 3 is a vertical section along dotted line III—III of FIG. 2.

DETAILED DESCRIPTION OF THE INVENTION

Figure 1:
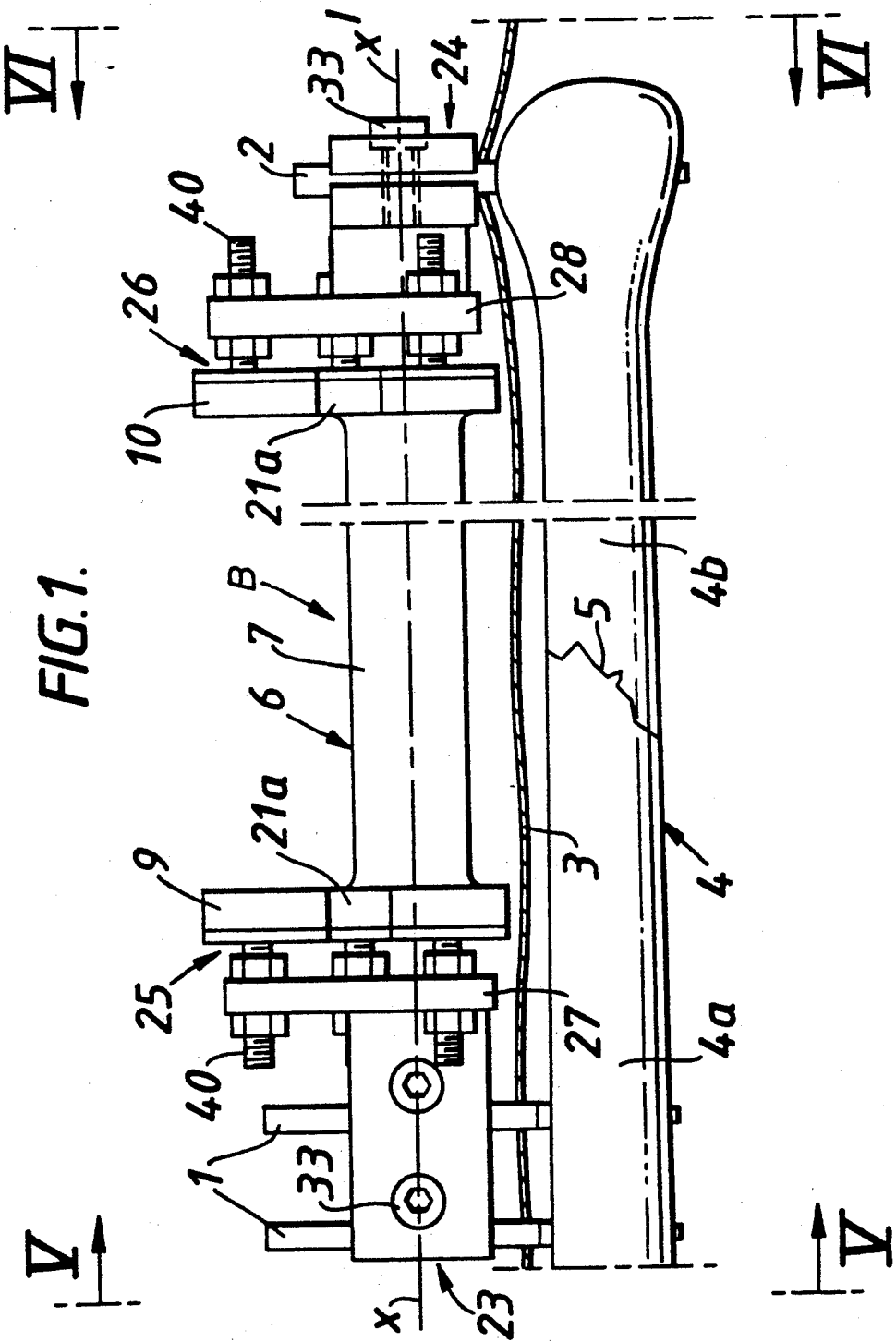
FIG. 1 is a view of the external brace in position holding and reducing a limb fracture.

According to the first application illustrated by FIGS. 1 through 3, the brace designated as a whole by reference B, is intended to connect rigidly groups of pins 1 and 2 implanted from outside a limb 3, a bone of which 4 is divided, following some traumatism, into two segments 4a and 4b on both sides of a fracture line 5. Pins 1 and 2 are implanted in the manner which is familiar to be screwed in segments 4a and 4b, respectively to form anchoring points linked by external brace B, which must assume the primary function of a positive, mechanical, firm, strong connection outside limb 3, and at least one secondary function of adjustment of relative alignment and direction between groups of pins 1 and 2, so that segments 4a and 4b can be placed relative to one another with bone 4 in a state of reconstitution. Since the function of adjustment of direction must be assumed, it therefore involves additionally a function of adjusting the gap between segments 4a and 4b.

To assume the above functions while offering the least possible lateral encumbrance as well as the option of taking X-rays, external brace B, comprises an elongated support 6 made up of two telescopic components 7 and 8 which it is advantageous to manufacture of an X-ray transparent material such as particularly a composite carbon fiber-, Aramide fiber-, or glass fiber-based material. Components 7 and 8 may consist of a tube and rod with complementary straight cross sections adhering to a precise fit tolerance such as, for example, $H7_86$. The straight cross sections may be circular or polygonal, which seems to be a preferred choice to establish an immovable angular alignment between telescopic components 7 and 8. In the case of circular sections, angular immobilizing devices may be provided between components 7 and 8 to work together relative to each other. Such devices may be formed of a channel or channels, for example, or a tongue and groove. The relative length of telescopic components 7 and 8 is selected with respect to the specific application and corresponds to the maximum range which may be encountered in practice in all cases of reduction, knitting and alignment of the so-called long bones.

The technique of manufacturing by machining or molding of telescopic components 7 and 8 is planned so that they each include a plate 9 and 10 at their opposite ends, the plane of which is transverse to axis x—x' common to telescopic components 7 and 8, Plates 9 and 10 are preferably circular in shape and formed respectively so that components 7 and 8 are offset in relation to center c of the plates as can be seen in FIG. 2. This arrangement makes it possible to reduce radial measurement r between axis x—x' and the local periphery of plates 9 and 10 and therefore have a positive, particularly strong connecting mechanism which can thus be placed, as is shown in FIG. 1, as near as possible to the outer surface of limb 3 in a direction which may be strictly parallel to the diaphysis of a fractured long bone as the example in FIG. 1 illustrates.

Telescopic components 7 and 8 are associated with a longitudinal adjusting and locking device 11. Such a device 11 is composed of a slide 12 engaged by two chucks 13 and 14 equipped with clamping mechanisms 15 and 16. Chucks 13 and 14, moreover, each have a finger 17, 18 intended to engage a recessed hole 19, 20 running from the periphery of plates 9 and 10, preferably, in the part of the latter angularly opposite telescopic components 7 and 8. Recessed holes 19 and 20 are preferably made from the bottom of recesses 21 and 21a made at the periphery of plates 9 and 10 to receive at least part of the bodies of chucks 13 and 14.

The adjusting device 11 described above makes it possible, after unscrewing screws 15 and 16, to release slide 12 and, therefore, to slide telescopic components 7 and 8 relative to each other to extend or retract until the spread position to be retained is reached. When it is, screws 15 and 16 are retightened to ensure, by means of slide 12, that plates 9 and 10 and telescopic components 7 and 8 are immobilized relative to each other, firmly and strongly.

Plates 9 and 10, with their opposite surfaces to those corresponding to telescopic components 7 and 8, are intended to hold two locking flanges 23 and 24 by means of two position-adjusting devices 25 and 26. Each flange has a plate 27, 28 extended by a chuck body 29, 30 each having an axis of symmetry y—y' normally placed coaxially to axis x—x'. Chuck bodies 29 and 30 are designed to include two clamping jaws 31 and 32 joined by clamping mechanisms 33 and providing immobilizing slots 34 between each other for pins 1 or 2. The plane of jaws 31 and 32 may be parallel to axis x—x', as shown for flange 23 according to FIG. 3, or perpendicular to that axis, as represented for flange 24.

Figure 4:
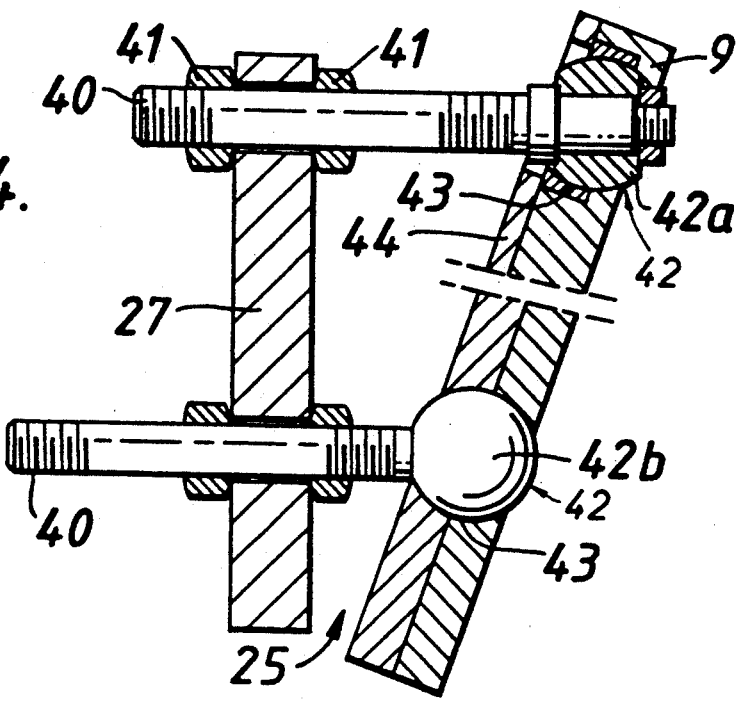
FIG. 4 is a vertical section showing, on a larger scale, a detail of an application of one of the components of the brace.
Figure 5:
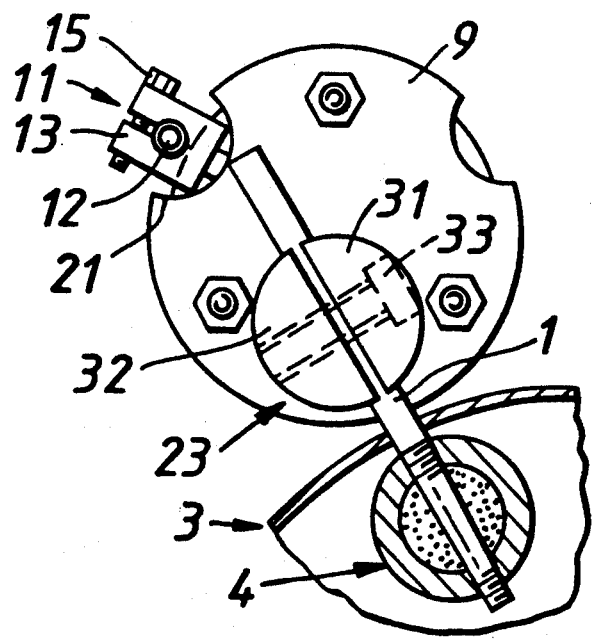
FIGS. 5 and 6 are cross sections along lines V—V and VI—VI of FIG. 1.
Figure 6:
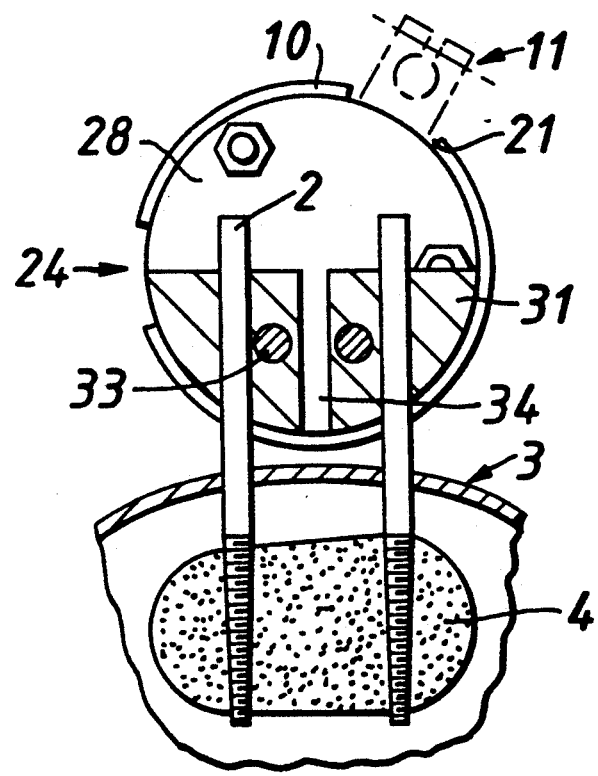
Figure 7:
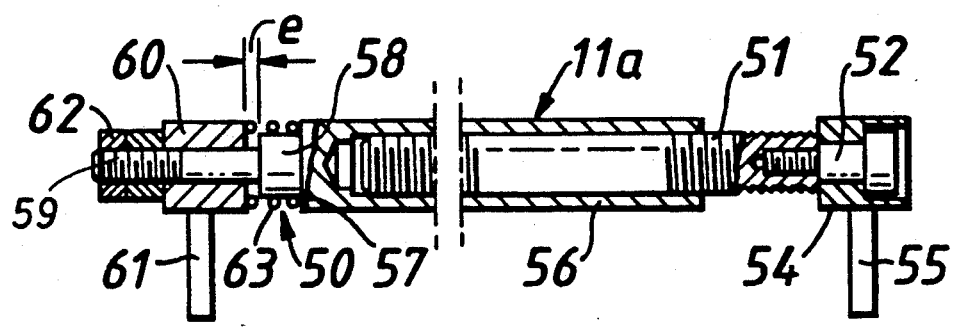
FIG. 7 is a partial vertical section illustrating an application variant of one of the components of the brace.

Position-adjusting devices 25 and 26 are identical in construction, and for that reason only one is described in what follows with reference to FIG. 4. Consideration should therefore be given to the fact that the same technical devices assigned the same references correspond to the second device.

FIG. 4, corresponding more particularly to device 25, shows that the position-adjusting device brings into play between plate 9 and plate 27 three angularly equidistant threaded rods 40 passing through plate 27 in a direction perpendicular to the plane of the latter, with respect to which they may be adjusted in length by means of locking mechanisms 41 such as a screw and counterscrew system. Each threaded rod 40 has a ball-type head 42 which is mounted in a complementary slot 43 presented by plate 9. Each ball 42 may be made up of an independent element joined to rod 40 as illustrated by reference 42a or, on the other hand, represent an integral part of rod 40, as illustrated by reference 42b. The relative capacity of rotation of ball 42 in slot 43 is maintained by a locking counterplate 44 immobilized on plate 9 by means of a screw or the like 45 (FIG. 2).

By means of nuts 41 it becomes possible to adjust the length of each rod 40 and, consequently, the measurement of spread between plate 9 and plate 27. A versatile positioning adjustment can therefore come into play to give plate 27 the adjustment exactly appropriate for plane y—y' of slots 34 to correspond to the direction of implantation of the pins in the bone segment.

After the implantation of pins 1 and 2, the brace may therefore be adjusted easily to make it possible for flanges 23 and 24 to fit over the groups of pins which are connected rigidly by the tightening of counternuts 41, screws 33 and chucks 13 and 14. These settings, of course, may always be adjusted by acting on the same technical mechanisms to complete the reduction of segments 4a and 4b to spread and bring about relative spatial orientation.

When adjustments have been made, final tightening of the various devices such as 15, 16, 41 and 33 makes it possible to maintain and guarantee with assurance over time the preferred orientations decided upon, so that segments 4a and 4b remain in a position of reduction favorable to the knitting of the fracture.

As is well known, the knitting of a fractured bone may with advantage involve a compression phase of the bone undergoing knitting by progressive resubjection to load favoring the strength of the immobilized bone. The external holding brace according to the invention makes the use of such a technique possible. Indeed, plates 9 and 10, especially because of the eccentric position of telescopic components 7 and 8, may, in the angular half opposite the latter, have two series of recesses such as 21, 21a equipped with recessed holes 19, 19a and 20, 20a. Thus it becomes possible, when immobilizing and when the time has come, to fit in recesses 21 and 21a substitution locking mechanism 11a incorporating an adjustable elastic shock absorber 50 with limited axial travel. Mechanism 11a consists, for example, of a threaded rod 51 mounted by means of an angular locking or release system 52 on a ring 54 extended by a finger 55 which can fit into one of the recessed holes 19a or 20a. Threaded rod 51 operates in conjunction with a screwed shaft 56 extending beyond a shoulder 57 with a cropped part 58 beyond which extends a rod 59 passing through a ring 60 extended radially by a finger 61 to be in a position to engage one of the recesses 19a, 20a. Rod 58 has at the end of it an axial system of adjustment 62 acting to bring compressive stress to bear on an elastic mechanism 63 surrounding the cropped part 58 to rest between shoulder 57 and ring 60. Adjustment by system 62 is designed to define between ring 60 and cropped part 58 a spread corresponding to a limited elastic deformation range e of spring 63.

When substitution locking mechanism 11a has been fitted and adjusted to plates 9 and 10, the main mechanism 11 may be removed.

Under these circumstances the holding brace can be used to put bone 4 under compressive stress by applying a load which at first is transmitted in the manner of a harness system to the brace and between plates 9 and 10, which are brought relatively closer corresponding to range e of absorption of the elastic shock absorber 50. When range e has been absorbed, shaft 56 is thrust positively against ring 60 and then reconstitutes the harness proper so as to bear the maximum compressive load beyond that accepted by shock absorber 50. Thus part of that load is taken by the bone as long as the range of absorption e has not been offset, which makes it possible, by properly selecting the characteristics of spring 63 and the adjustment afforded by system 62, to subject the bone being knit together to a partial, adjustable and progressive compressive load.

Consideration must be given to the fact that this function does not do away with the previous functions of maintaining alignment, as the only degree of freedom afforded by substitution locking mechanism 11a is parallel to axis x—x'.

The external brace according to the invention may also, because of its composition, be used for the application of the method of stretching bones sometimes used when a difference in length is found between homologous bones of two limbs. Such a difference in length may result from a growth defect or an accidental loss of substance. The stretching technique, during knitting together, consists of permitting a slight, relative, progressive gap between bone segments such as 4a and 4b separated by a line of fracture 5.

Figure 8:
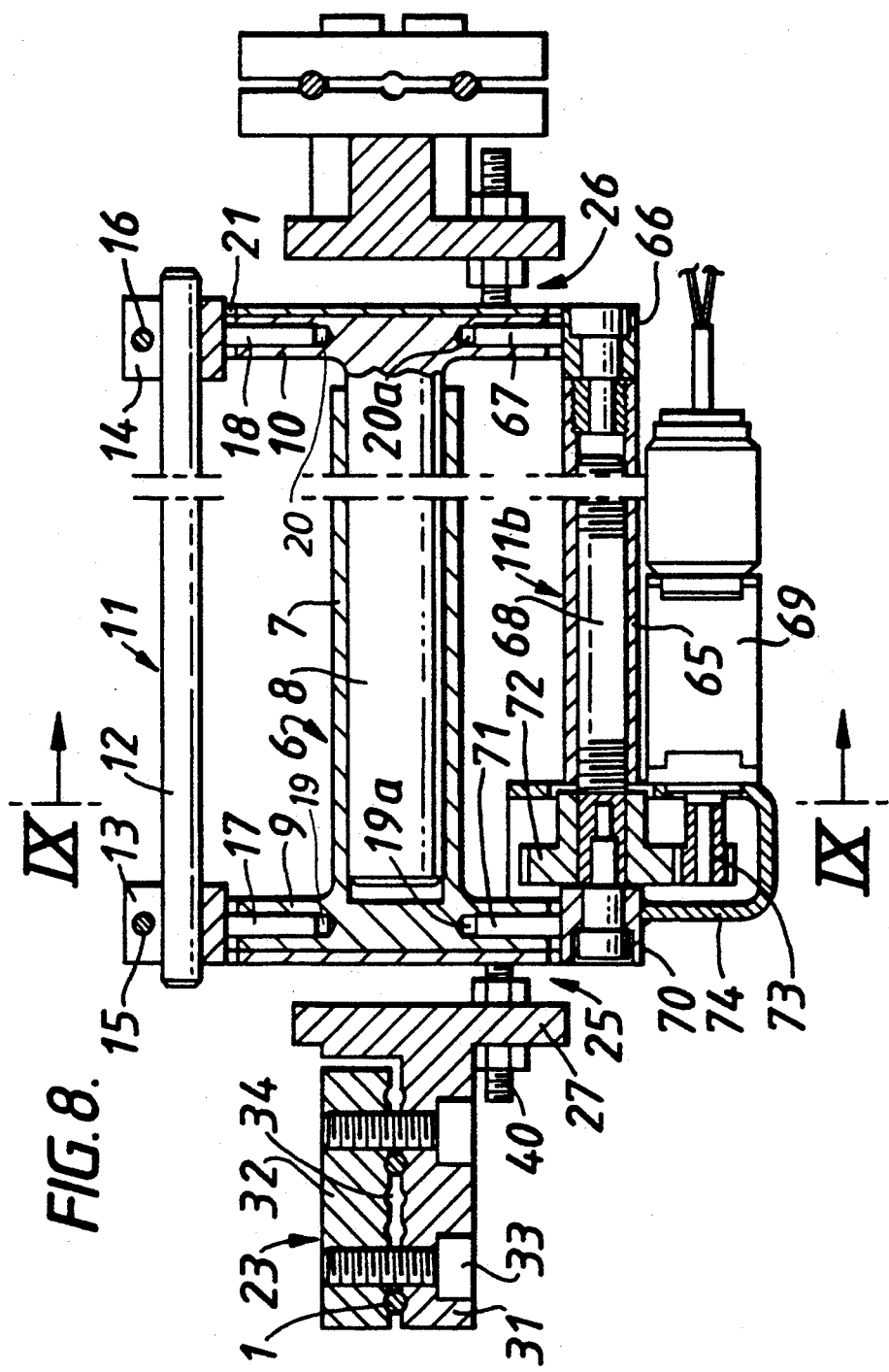
FIG. 8 is a vertical section similar to FIG. 3 showing an application variant of the brace along dotted line VIII—VIII in FIG. 9.
Figure 9:
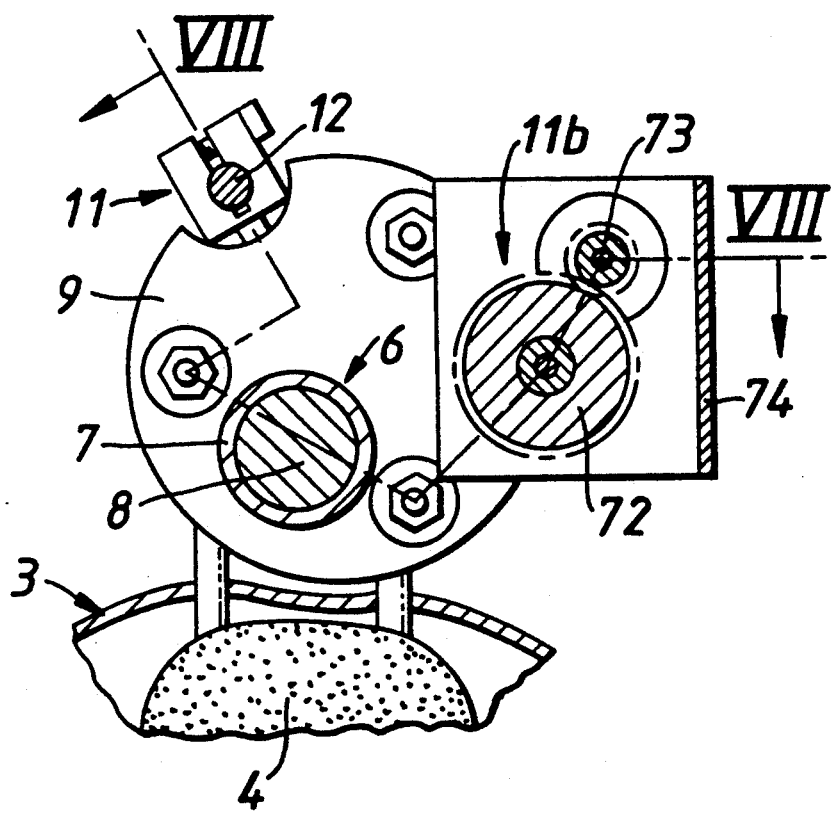
FIG. 9 is a cross section along line IX—IX in FIG. 8.

To make it possible to apply such a knitting-together technique, locking and adjustment device 11 or 11a is replaced by a device 11b as represented by FIGS. 8 and 9. Such a device as 11b is designed to adapt to plates 9 and 10 either alone or in combination with device 11 described with reference to FIGS. 1 and 2.

Device 11b is composed mainly of a jack of the micrometer screw type comprising a screwed cylinder 65 immobilized on a ring 66 extended radially by a finger 67 designed to engage one of the recessed holes 19, 19a, 20, 20a. Screwed cylinder 65 attached to and protruding from ring 66 extends parallel to axis x—x' to work in conjunction with a screw 68 associated with a motorized reducer unit 69 of the electric type driving it. Screw 68 is preferably mounted with the possibility of rotation on a ring 70 extended radially with a finger 71 which may be mounted in one of the recessed holes 19, 19a, 20, 20a. Screw 68 has on it, for example, a gear wheel 72 permanently engaging a gear wheel 73 fitted to the driven shaft of motorized reducer unit 69 which may be installed on a casing on ring 70.

The intermittent supply of motorized reducer unit 69 allows screw 68 to be turned in the direction corresponding to the displacement sought to bring together or, on the other hand, push apart plates 9 and 10 when a stretching phase is desired.

The invention is not limited to the examples described and represented, since various modifications of it may be introduced without departing from the scope of it.

I claim:

1. External holding and reducing brace for bone fractures, of the type comprising an elongated support (6) made up of two telescopic components (7, 8), a device (11) for adjusting and locking those telescopic components, two end flanges (23, 24) fitted to the opposite ends of those components by means of position-adjusting devices (25, 26) and movable pins (1, 2) gripped by the flanges to point in a direction different from that if axis x—x' of the elongated support and designed to be screwed from outside the limb into the fractured bone (4) and on either side of the line of fracture (5), characterized by the fact that:

the telescopic components (7, 8) are made of an X-ray transparent material and form two transverse plates (9 and 10) at their opposite ends;

the locking device (11) is composed of a slide (12) working in conjunction with two chucks (13 and 14) adapted to the periphery of the plates;

the position-adjusting devices, for each flange, are made up of three threaded rods (40), angularly equidistant, individually adjustable in length and mounted by means of three ball-and-socket joints in the corresponding plate.

2. Brace according to claim 1, characterized by the fact that the telescopic components (7, 8) are eccentric with respect to the plates (9 and 10) which bear flanges (23 and 24) of which the axes y—y' of symmetry are coaxial with axis x—x' of the telescopic components.

3. Brace according to claim 1 or 2, characterized by the fact that the telescopic components (7 and 8) work together by means of an angular immobilization device.

4. Brace according to claim 1, characterized by the fact that the two transverse plates (9 and 10) have recesses (19 and 20) radial to the periphery of the transverse plates and the two chucks (13 and 14) are perpendicular to the axis of the slide and have fingers (17 and 18) fitting into the recesses (19 and 20).

5. Brace according to claim 1, characterized by the fact that at least one of the flanges has a plate (27) holding a chuck body (29) forming slots (34) for locking pins, the latter being situated in a common plane y—y' passing along the axis of the telescopic components for a neutral position in which plate (27) is parallel to the corresponding plate.

6. Brace according to claim 1 or 5, characterized by the fact that least one of the flanges has a plate (28) holding a chuck body (30) forming slots (34) for locking pins, the latter being situated in a common plane perpendicular to the axis of the telescopic components for a neutral position in which the plate is parallel to the corresponding plate.

7. Brace according to claim 1 or 4, characterized by the fact that the slide (12) has an elastic shock absorber (50) with adjustable limited travel.

8. Brace according to claim 1, characterized by the fact that the device (11) for adjusting the telescopic components (7 and 8) is composed of a micrometer screw jack (11b) fitted between the plates.

9. Brace according to claim 8, characterized by the fact that the micrometer screw jack (11b) is associated with an electric motorized reducer unit (69) borne by the elongated support.

10. Brace according to claim 9, characterized by the fact that the micrometer screw jack has, on the one hand, a screwed cylinder (65) fixed to and fitted so as to protrude from one of the plates to extend parallel to axis x—x' of the telescopic components (7 and 8) and, on the other hand, a casing (74) supporting a screw (68) and a reversible driving motor (69), the casing being fitted to the second plate so that the screw works in conjunction with the cylinder into which it is screwed.

11. An external holding and reducing brace for a bone fracture in a limb, comprising:
an elongated support having first and second telescopic components;
means for adjusting and locking said first and second telescopic components;
a first end flange cooperatively connected to said first telescopic component;
a second end flange cooperatively connected to said second telescopic component;
means for positioning and adjusting said end flanges relative to said telescopic components, said positioning and adjusting means for each said end flange including a plurality of rods pivotably connected to said telescopic component and means for individually adjusting the locking mechanisms in length to alter the angular relationship of said end flange relative to said telescopic components; and
a plurality of first movable pins and a plurality of second movable pins gripped by said first and second end flanges, respectively, to point in a direction different from that of the longitudinal axis of said elongated support, said movable pins adapted to be screwed from outside the limb into the fractured bone on either side of the bone fracture.

12. The brace according to claim 11, wherein said elongate support includes first and second transverse plates at opposite ends of said elongate support, said first transverse plate attached to said first telescopic component and said second transverse plate attached to said second telescopic component.

13. The brace according to claim 12, wherein said adjusting and locking means comprises:
a first chuck attached to said first transverse plate, said first chuck having a through bore and a first locking screw;
a second chuck attached to said second transverse plate, said second chuck having a through bore and a second locking screw; and
a slide member slidably extending through the through bores of said first and second chucks;
wherein said locking pins are tightened to clamp said slide member to said chucks and lock the length of said elongate support.

14. The brace according to claim 13, wherein each said transverse plate includes a radial hole in the periphery of said transverse plate and each said chuck includes a finger received in said radial hole for securing said adjusting and locking means to said elongate support.

15. The brace according to claim 12, wherein said telescopic components are eccentric with respect to said transverse plates and said end flanges are substantially concentric with said telescopic components.

16. The brace according to claim 12, wherein each said end flange includes a plate attached to a flange chuck body having slots for said movable pins with said end flange plates being substantially parallel to said transverse plates.

17. The brace according to claim 16, wherein said plurality of first movable pins are situated in a common plane perpendicular to said first end flange plate.

18. The brace according to claim 16, wherein said plurality of second movable pins are situated in a common plane parallel to said second end flange plate.

19. The brace according to claim 16, wherein said plurality of first movable pins are situated in a common plane substantially perpendicular to a common plane of said plurality of second movable pins.

20. The brace according to claim 12, wherein said adjusting and locking means comprises a micrometer screw jack connected to and extending between said transverse plates.

21. The brace according to claim 20, wherein said micrometer screw jack comprises:
a screwed cylinder fixed to and fitted so as to protrude from said first transverse plate to extend parallel to the longitudinal axis of said elongate support;
a casing fitted to said second transverse plate; and
a screw member supported at a first end by said casing and having a second end received by said screwed cylinder.

22. The brace according to claim 21, wherein said micrometer screw jack further includes an electric motorized reducer unit to rotate said screw member in the direction of the displacement of said transverse plates sought.

23. The brace according to claim 11, wherein said telescopic components are immobilized from angular rotation relative to one another.

24. The brace according to claim 11, wherein said adjusting and locking means includes a means for allowing limited axial travel of said elongate support resulting from external forces acting on the limb.

25. The brace according to claim 24, wherein said limited travel means is a shock absorber having an adjustable limited travel.

26. The brace according to claim 11, wherein said telescopic components are made of an X-ray transparent material.

27. An external holding and reducing brace for a bone fracture in a limb, comprising:
an elongated support having first and second telescopic components which are made of an X-ray transparent material, said elongate support including first and second transverse plates at opposite ends of said elongate support, said first transverse plate attached to said first telescopic component and said second transverse plate attached to said second telescopic component;

means for adjusting and locking said first and second telescopic components;

a first end flange cooperatively connected to said first telescopic component;

a second end flange cooperatively connected to said second telescopic component;

means for positioning and adjusting said end flanges relative to said telescopic components, said positioning and adjusting means for each said end flange including three threaded rods pivotably connected to said elongate support by ball-and-socket joints and individually adjustable to alter the angular relationship of said end flange relative to said telescopic components; and a plurality of first movable pins and a plurality of second movable pins gripped by said first and second end flanges, respectively, to point in a direction different from that of the longitudinal axis of said elongated support, said movable pins adapted to be screwed from outside the limb into the fractured bone on either side of the bone fracture.

* * * * *